(12) United States Patent
Landt

(10) Patent No.: US 6,632,844 B1
(45) Date of Patent: Oct. 14, 2003

(54) METHODS AND COMPOSITIONS FOR PRESERVING GLUCOSE LEVEL IN BLOOD SPECIMENS

(75) Inventor: Michael Landt, St. Louis, MO (US)

(73) Assignee: Washington University, St. Louis, MO (US)

( * ) Notice: Subject to any disclaimer, the term of this patent is extended or adjusted under 35 U.S.C. 154(b) by 260 days.

(21) Appl. No.: 09/816,493

(22) Filed: Mar. 23, 2001

Related U.S. Application Data

(60) Provisional application No. 60/192,971, filed on Mar. 29, 2000.

(51) Int. Cl.$^7$ .............................................. A61K 31/11
(52) U.S. Cl. ........................................... 514/693; 435/2
(58) Field of Search ............................... 435/2; 514/693

(56) References Cited

U.S. PATENT DOCUMENTS

| | | | | |
|---|---|---|---|---|
| 4,030,888 | A | 6/1977 | Yamamoto et al. | 23/253 |
| 4,040,785 | A | 8/1977 | Kim et al. | 23/230 |
| 4,054,488 | A | 10/1977 | Marbach | 195/1.8 |
| 4,135,883 | A | 1/1979 | McNeil et al. | 422/72 |
| 4,353,987 | A | 10/1982 | Wolf | 435/147 |
| 4,356,172 | A | 10/1982 | Nakao et al. | 424/101 |
| 4,780,419 | A | 10/1988 | Uchida et al. | 436/176 |
| 4,833,090 | A | 5/1989 | Liss et al. | 436/14 |
| 4,933,145 | A | 6/1990 | Uchida et al. | 422/61 |
| 5,037,738 | A | 8/1991 | Lamos et al. | 435/12 |
| 5,156,974 | A | 10/1992 | Grossman et al. | 436/69 |
| 5,286,625 | A | 2/1994 | Tanaka et al. | 435/18 |
| 5,360,011 | A | 11/1994 | McCallister | 128/763 |
| 5,583,432 | A | 12/1996 | Barnes | 324/204 |
| 5,645,710 | A | 7/1997 | Shieh | 205/778 |
| 5,695,949 | A | 12/1997 | Galen et al. | 435/14 |
| 5,788,652 | A | 8/1998 | Rahn | 600/577 |
| 5,843,692 | A | 12/1998 | Phillips et al. | 435/14 |
| 5,930,791 | A | 7/1999 | Leu | 707/8 |
| 5,935,802 | A | 8/1999 | Lind | 435/13 |
| 5,955,371 | A | 9/1999 | Ikeda et al. | 436/18 |
| 6,027,692 | A | 2/2000 | Galen et al. | 422/82.05 |

FOREIGN PATENT DOCUMENTS

| | | |
|---|---|---|
| EP | 0367271 | 5/1990 |
| JP | 61015838 | 1/1986 |

OTHER PUBLICATIONS

Baer and Fischer, *Scinece*, 88:108 (1938).
Banez and Bacaling, *Arch. Pathol., Lab. Med.*, 112(9):885–8 (1988).
Best and Thornalley, *Biochem, Pharmacol.*, 57:583–8 (1999).
Brugnara et al., *Am. J. Clin. Pathol.*, 102(5):623–32 (1994).
Bueding and Goldfarb, *J. Biol. Chem.*, 141:539–44 (1942).
Carulli et al., *Int. J. Clin. Lab. Res.*, 25(4):216–21 (1995).
Chan et al., *Clin. Chem.*, 35:315–7 (1989).
Chan et al., *Clin. Chem.*, 38:411–3 (1992).
Denis and Beven, *J. Lab. Clin. Med.*, 9:674–9 (1924).
Dietzler and Smith, Carbohydrates. In: Sonnenwirth AC, Jarett L, eds., Gradwohl's Clinical Laboratory Methods and Diagnosis, vol. I, 8$^{th}$ ed. St. Louis Louis, Toronto, London: CV Mosby Co., 1980:210–49).
Floridi et al., *J. Natl. Cancer. Inst.*, 66(3):497–9 (1981).
Goto et al., *Am. J. Vet. Res.*, 55:291–4 (1994).
Hall and Cook *Clin. Chem.*, 28:387–8 (1982).
Hartmann et al., *FEBS Lett.*, 93(2):339–42 (1978).
Ho et al., *Clin. Chem.*, 37:477 (1991).
Innanen et al., *J. Pediatr.* 130:151–5 (1997).
Krebs and Lund, *Biochem. J.*, 98:210–4 (1966).
Lin et al., *Clin Chem.*, 22:2031–3 (1976).
Meites and Saniel–Banrey, *Clin. Chem.*, 25:531–4 (1979).
Nakashima et al., *Clin. Chem.*, 33:708–10 (1978).
Perlin, Methods in Carbohydrate Chemistry, 1:61 (1962).
Pictet and Barbier, *Helv. Chim. Acta*, 4:924 (1921).
Sallee et al., *J. Am. Vet. Med. Assoc.*, 196(2):307–12 (1990).
Sidebottom et al., *Clin. Chem.*, 28:190–2 (1982).
Takekawa et al., *Acta Haematol.*, 100(3):130–6 (1998).
Thornalley and Stern, *Biochem. Biophys. Acat*, 804:308–23 (1984).
van Dijck and Lievens, *Clin. Chem.*, 37:1308–9 (1991).
Witzemann, *J. Am. Chem. Soc.*, 36,:2227 (1914).

Primary Examiner—Jean C. Witz
(74) Attorney, Agent, or Firm—Morrison & Foerster LLP

(57) ABSTRACT

The invention relates to methods and compositions for preserving blood samples. In particular, a method for stabilizing glucose level in a blood sample is provided, which method comprises adding an effective amount of glyceraldehyde to a blood sample, whereby glucose level in said blood sample remains substantially constant for a period of time. Kits and combinations for stabilizing glucose level in a blood sample are also provided.

23 Claims, 3 Drawing Sheets

METHODS AND COMPOSITIONS FOR PRESERVING GLUCOSE LEVEL IN BLOOD SPECIMENS

This application claims priority of U.S. Provisional Patent Application Serial No. 60/192,971, filed Mar. 29, 2000 under 35 U.S.C. §119(e). The disclosure of the above-identified application is incorporated herein by reference in its entirety.

TECHNICAL FIELD

The invention relates to methods and compositions for preserving blood samples. In particular, a method for stabilizing glucose level in a blood sample is provided, which method comprises adding an effective amount of glyceraldehyde to a blood sample, whereby glucose level in said blood sample remains substantially constant for a period of time. Kits and combinations for stabilizing glucose level in a blood sample are also provided.

BACKGROUND ART

Glucose is one of the most commonly measured components of blood, because of the central role of glucose in metabolism and the high prevalence of diseases of glucose homeostasis. A continuing problem in the accurate measurement of glucose is the loss of glucose from specimens due to glycolysis by erythrocytes during transport and processing (Sidebottom et al., Clin. Chem., 28:190–2 (1982)). In recent years, this phenomenon has been more evident, as laboratory services have consolidated and many more specimens are transported to distant laboratories for analysis. Several approaches have been proposed to minimize glycolysis, including centrifugation/decantation of plasma immediately after specimen collection (Sidebottom et al., Clin. Chem., 28:190–2 (1982), refrigeration/cooling on ice during transport (Lin et al., Clin. Chem., 22:2031–3 (1976)), addition of anti-glycolytic agents such as iodoacetate (Bueding and Goldfarb, J. Biol. Chem., 141:539–44 (1942)), fluoride (Denis and Beven, J. Lab. Clin. Med., 9:674–9 (1924)) or mannose (Nakashima et al., Clin. Chem., 33:708–10 (1987)) to the collection tubes, and the use of glucose analyzers designed for near-patient testing, at the bedside (Innanen et al., J. Pediatr., 130:151–5 (1997)). All of these approaches are in current use, and the use of fluoride in blood collection tubes is prevalent in circumstances where substantial delay between collection and analysis is anticipated, but all have significant limitations (for review, see Dietzler and Smith, Carbohydrates. In: Sonnenwirth A C, Jarett L, eds. Gradwohl's Clinical Laboratory Methods and Diagnosis. Vol I, 8$^{th}$ ed. St. Louis, Toronto, London: CV Mosby Co., 1980:210–49). To various degrees, these approaches are limited in efficacy by either incomplete inhibition of glycolysis, interference in testing for co-analytes (electrolytes, creatinine, urea, etc.), disturbance of cellular integrity such as hemolysis or promotion of leakage of intracellular potassium.

The ideal approach for eliminating glycolytic loss would provide reasonably stable glucose levels for a period needed for transport to a centralized laboratory, avoid costly near-patient centrifugation/special handling/analysis, and yield a specimen that is suitable for analysis of many other common analytes so that separate collection of specimen for those analytes is not necessary. From a practical standpoint, the best way to achieve this goal is discovery of an antiglycolytic agent that can be added to collection tubes but does not alter cellular integrity or interfere in common analytical methodologies. Such an agent should also be effective at low concentration (minimizing volume addition to avoid dilution errors), dissolve rapidly during the collection process, be non-toxic, be stable in the room-temperature storage environment of blood collection devices, and be inexpensive. Glyceraldehyde has these properties as an additive in blood collection devices.

DISCLOSURE OF THE INVENTION

The invention provides methods and compositions for stabilizing glucose level in a blood sample using glyceraldehyde. Kits and combinations for stabilizing glucose level in a blood sample containing glyceraldehyde are also provided.

In one aspect, the invention is directed to a method for stabilizing glucose level in a blood sample, which method comprises adding an effective amount of glyceraldehyde to a blood sample, whereby glucose level in said blood sample remains substantially constant for a period of time.

D-glyceraldehyde, 1-glyceraldehyde, or racemic mixture of d,1-glyceraldehyde can be used. Preferably, 1-glyceraldehyde is used.

Suitable amounts of glyceraldehyde should be used in the methods. If racemic mixture of d,1-glyceraldehyde is used, the final concentration of the racemic mixture of d,1-glyceraldehyde in the blood sample is preferably from about 0.9 to about 20 mM. More preferably, the final concentration of the racemic mixture of d,1-glyceraldehyde in the blood sample is from about 5 to about 10 mM. If 1-glyceraldehyde is used, the final concentration of the 1-glyceraldehyde in the blood sample is preferably from about 0.65 to about 10 mM. More preferably, the final concentration of the 1-glyceraldehyde in the blood sample is from about 2.5 to about 5 mM.

The present method can be used for stabilizing glucose level in any blood sample. Preferably, the blood sample is a whole blood, plasma or serum sample. More preferably, the whole blood sample is a heparinized whole blood sample.

The present method can be used for stabilizing glucose level in a blood sample with any concentration of glucose. Preferably, the starting glucose concentration in the blood sample is from about 0 to about 100 mM. More preferably, the starting glucose concentration in the blood sample is from about 3.9 mM to about 13.4 mM.

The present method can be used for stabilizing glucose level in a blood sample so that the glucose level in said blood sample remains substantially constant for a period of time. Sufficient amount of glyceraldehyde can be used so that the starting glucose concentration does not decrease by more than 5%, and preferably, 2%. Similarly, sufficient amount of glyceraldehyde can be used so that the glucose level in the blood sample remains substantially constant for at least about 16 hours, and preferably for at least about 8 hours.

The blood sample that is treated with the present method, i.e., with added glyceraldehyde, can be subjected to a "metabolism" assay. Such metabolism assay can be used in assaying molecules important in metabolism such as inorganic molecules, e.g., $O_2$ or $CO_2$ or inorganic ions such as sodium, potassium, magnesium, calcium, chloride, iron, copper, zinc, manganese, cobalt, iodide, molybdenum, vanadium, nickel, chromium, fluoride, silicon, tin, boron or arsenic ions. Such metabolism assay can also be used in assaying organic molecules including amino acids, peptides, nucleosides, nucleotides, oligonucleotides, vitamins, monosaccharides, oligosaccharides or lipids. Class of molecules, e.g., proteins, nucleic acids, lipids or carbohydrates can also be assayed.

Preferably, the metabolism assay is used in assaying ions such as sodium, potassium, chloride and calcium ions, glucose, creatinine, urea, bilirubin, albumin, alkaline phosphatase activity, aspartate aminotransferase (AST), total protein and total $CO_2$. Also preferably, the metabolism assay is operated on an automated analyzer such as Ortho-Clinical Diagnostics Vitros 250, Dade Behring RxL and Hitachi 747 analyzer.

In another aspect, a kit for stabilizing glucose level in a blood sample is provided, which kit comprises: a) an effective amount of glyceraldehyde; and b) an instruction indicating that said kit is used for stabilizing glucose level in a blood sample.

In still another aspect, a combination for stabilizing glucose level in a blood sample is provided, which combination comprises: a) an effective amount of glyceraldehyde; and b) an effective amount of an anti-glycolytic agent that is not glyceraldehyde. This combination is useful in a method for stabilizing glucose level in a blood sample, which method comprises adding an effective amount of glyceraldehyde and an effective amount of an anti-glycolytic agent that is not glyceraldehyde to a blood sample, whereby glucose level in said blood sample remains substantially constant for a period of time. In this method, the glyceraldehyde and the anti-glycolytic agent can be added to the blood sample simultaneously or sequentially.

In yet another aspect, a combination for preserving a blood sample for a further analysis is provided, which combination comprises: a) an effective amount of glyceraldehyde; and b) an effective amount of a blood-preserving agent. This combination is useful in a method for preserving a blood sample for a further analysis, which method comprises adding an effective amount of glyceraldehyde and an effective amount of a blood-preserving agent to a blood sample, whereby the quality of said blood sample is substantially preserved for a further analysis. In this method, the glyceraldehyde and the blood-preserving agent can be added to the blood sample simultaneously or sequentially.

MODES OF CARRYING OUT THE INVENTION

A. Definitions

Figure 1:
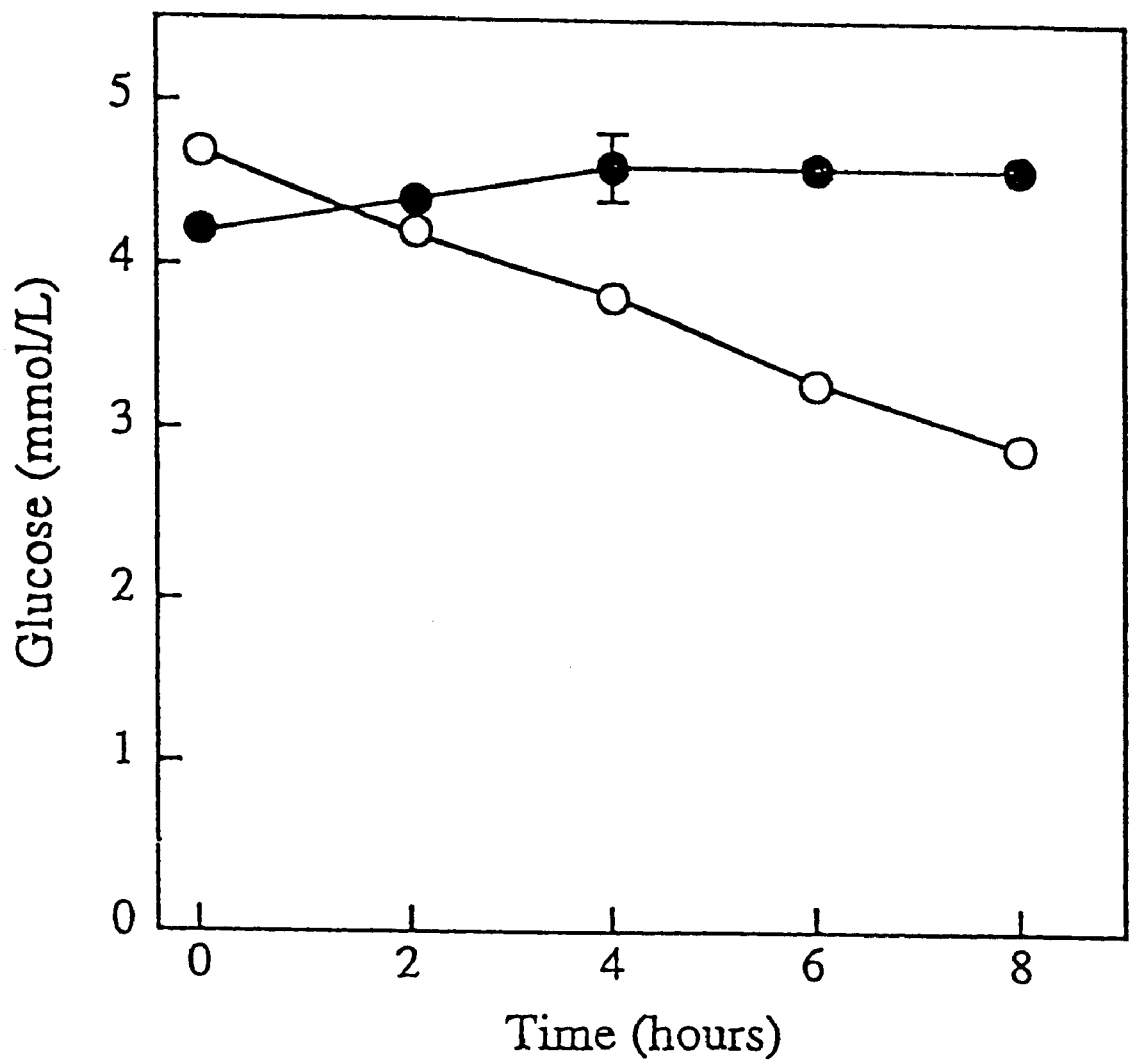
FIG. 1: Time course of glucose disappearance in the absence (○-○) and the presence (●-●) of 10 mmol/L d,1-GA. Error bars are shown for triplicate replicates where the error exceeds the size of the symbols used.

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails over the definition that is incorporated herein by reference.

As used herein, "a" or "an" means "at least one" or "one or more."

As used herein, "glyceraldehyde" refers to, preferably in a physiologically or pharmaceutically acceptable form, glyceraldehyde of the structure below, and prodrugs, salts, esters or other derivatives of glyceraldehyde known to those of skill in the art. For purposes herein, glyceraldehyde has the following structure:

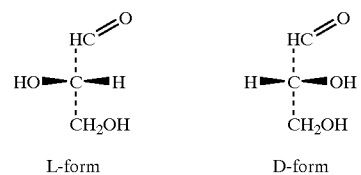

L-form          D-form

The term "glyceraldehyde" encompasses all physiologically or pharmaceutically active species of glyceraldehyde, or solutions thereof, or mixtures thereof. The term "glyceraldehyde" also encompasses hydrated versions, such as aqueous solutions, hydrolyzed products or ionized products of these compounds; and these compounds may contain different number of attached water molecules. Glyceraldehyde can exist as one of the two isomers, d-, or 1-glyceraldehyde, a racemic mixture of the two isomers, or a mixture of the two isomers in uneven proportion.

As used herein, "blood" refers to the "circulating tissue" of the body; the fluid and its suspended formed elements that are circulated through the heart, arteries, capillaries, and veins. "Blood" also refers to the means by which 1) oxygen and nutritive materials are transported to the tissues, and 2) carbon dioxide and various metabolic products are removed for excretion. Blood consists of a pale yellow or gray-yellow fluid, plasma, in which are suspended red blood cells (erythrocytes), white blood cells (leukocytes) and platelets.

As used herein, "whole blood" refers to the blood drawn from a selected donor and may contain an anticoagulant such as citrate ion, heparin or EDTA.

As used herein, "plasma" refers to the proteinaceous fluid (noncellular) portion of the blood, as distinguished from the serum obtained after coagulation.

As used herein, "serum" refers to the fluid portion of the blood obtained after removal of the fibrin clot and blood cells.

As used herein, "an effective amount of glyceraldehyde" refers to an amount of glyceraldehyde that, when added to a blood sample, maintains the glucose concentration in the blood sample at as least 50% of its initial concentration for a desired period of time. Preferably, the amount of glyceraldehyde maintains the glucose concentration at as least 60%, 70%, 80%, 90%, 95%, 98%, 99% and 100% of its initial concentration.

As used herein, "metabolism" refers to the sum of chemical and physical changes in tissue, consisting of anabolism, those reactions that convert small molecules into large, and catabolism, those reactions that convert large molecules into small, including both endogenous large molecules as well as biodegradation of xenobiotics.

As used herein, "metabolism assay" refers to an assay for any molecule, small or large one, that is involved in metabolism.

As used herein, "glycolysis" refers to the energy yielding conversion of D-glucose to lactic acid.

As used herein, "anti-glycolytic agent" refers to a substance that inhibits or decreases the rate of glycolysis. For the purposes herein, glyceraldehyde is considered an anti-glycolytic agent.

As used herein, "blood-preserving agent" refers to a substance that maintains the quality of a blood sample for its intended uses such as storage, processing, transportation, analysis and clinical uses including transfusion. For the purposes herein, glyceraldehyde is not considered a blood-preserving agent.

For clarity of disclosure, and not by way of limitation, the detailed description of the invention is divided into the subsections that follow.

B. Glyceraldehyde

Chemically, glyceraldehyde is 2,3-dihydroxypropanal. Chemical synonyms of glyceraldehyde include glyceric aldehyde and α,β-dihydroxypropionaldehyde. For purposes herein, the name "glyceraldehyde" is used herein, although all such chemical synonyms are contemplated.

Glyceraldehyde can be prepared according to methods known in the art. For example, DL-glyceraldehyde together with its isomer dihydroxyacetone can be obtained from glycerol by mild oxidation with hydrogen peroxide and ferrous salts as catalysts (Witzemann, *J. Am. Chem. Soc.*, 36,:2227 (1914)). The two isomers are convertible into another through a common enediol resulting from the migration of hydrogen atoms (Lobry de Bruyn van Eckenstein rearrangement). The two forms have been obtained through the action of nitrous acid on the corresponding form of 3-amino-2-hydroxypropanal (Wohl, Momber, *Ber.*, 47:3346 (1914); Pictet, Barbier, *Helv. Chim. Acta,* 4:924 (1921); cf. Baer, Fischer, *Science,* 88:108 (1938)). Preparation of L-glyceraldehyde from L-sorbose and of D-glyceraldehyde from D-fructose is also disclosed in Perlin, *Methods in Carbohydrate Chemistry,* 1:61 (1962).

In addition, glyceraldehyde can be prepared according to the process disclosed in U.S. Pat. No. 4,353,987, which process comprises contacting glycerol with methanol dehydrogenase until a substantial amount of glyceraldehyde is produced, and recovering the glyceraldehyde. U.S. Pat. No. 4,353,987 also discloses a microbiological process for preparing glyceraldehyde which comprises cultivating a methylotrophic bacterium, and contacting said bacterium with glycerol until a substantial amount of glyceraldehyde is produced, and recovering the glyceraldehyde.

Further, glyceraldehyde, whether the racemic mixture or each of the isomers, can be obtained from a commercial source such as Sigma Chemical Co. and Fisher Scientific, etc.

C. Methods for Stabilizing Glucose Level in a Blood Sample Using Glyceraldehyde

The invention relates to a method for stabilizing glucose level in a blood sample, which method comprises adding an effective amount of glyceraldehyde to a blood sample, whereby glucose level in said blood sample remains substantially constant for a period of time.

D-glyceraldehyde, 1-glyceraldehyde, racemic mixture of d,1-glyceraldehyde or a mixture of the two isomers in uneven proportion can be used. Preferably, 1-glyceraldehyde is used.

Suitable amounts of glyceraldehyde should be used in the methods. If a racemic mixture of d,1-glyceraldehyde is used, the final concentration of the racemic mixture of d,1-glyceraldehyde in the blood sample is preferably from about 0.9 to about 20 mM. More preferably, the final concentration of the racemic mixture of d,1-glyceraldehyde in the blood sample is from about 5 to about 10 mM. If 1-glyceraldehyde is used, the final concentration of the 1-glyceraldehyde in the blood sample is preferably from about 0.65 to about 10 mM. More preferably, the final concentration of the 1-glyceraldehyde in the blood sample is from about 2.5 to about 5 mM.

The present method can be used for stabilizing glucose level in any blood sample. Preferably, the blood sample is a whole blood, plasma or serum sample. More preferably, the whole blood sample is a heparinized whole blood sample.

The present method can be used for stabilizing glucose level in a blood sample with any concentration of glucose. Preferably, the starting glucose concentration in the blood sample is from about 0 to about 100 mM. More preferably, the starting glucose concentration in the blood sample is from about 3.9 mM to about 13.4 mM.

The present method can be used for stabilizing glucose level in a blood sample so that the glucose level in said blood sample remains substantially constant for a period of time. Sufficient amount of glyceraldehyde can be used so that the starting glucose concentration does not decrease by more than 5%, and preferably, 2%. Similarly, sufficient amount of glyceraldehyde can be used so that the glucose level in the blood sample remains substantially constant for at least about 16 hours, and preferably for at least about 8 hours.

The present method can be used for stabilizing glucose level in any blood sample. Blood samples can be collected or prepared according to the methods known in the art including the methods and/or devices disclosed in U.S. Pat. Nos. 5,788,652 and 5,360,011.

U.S. Pat. No. 5,788,652 discloses a blood sample collection device. The blood sample collection device includes an outer shell, a spring activated specialty needle for creating an incision in the patient where the blood sample is to be collected and a partially evacuated blood collection tube that is slidingly received in the blood sample collection device.

U.S. Pat. No. 5,360,011 discloses a blood sample collection kit having a syringe body, an open lumen needle, an elongated vacuum plunger for use with the syringe, and a pulling flange, a rubber sleeve covered transfer needle and screw threads at a distal end of the plunger for receiving a blood tube holder and a vacuum-type blood sample collection tube. The kit provides easy blood collection and blood transfer.

D. Uses of Blood Samples Preserved by Glyceraldehyde

The blood sample that is treated with the present method, i.e., with added glyceraldehyde, can be subjected to a metabolism assay. Such metabolism assay can be used in assaying molecules important in metabolism such as inorganic molecules, e.g., $O_2$ or $CO_2$ or inorganic ions such as sodium, potassium, magnesium, calcium, chlorine, iron, copper, zinc, manganese, cobalt, iodine, molybdenum, vanadium, nickel, chromium, fluorine, silicon, tin, boron or arsenic ions. Such metabolism assay can also be used in assaying organic molecules including amino acids, peptides, nucleosides, nucleotides, oligonucleotides, vitamins, monosaccharides, oligosaccharides or lipids. Class of molecules, e.g., proteins, nucleic acids, lipids or carbohydrates can also be assayed.

Non-limiting examples of amino acids include D- or L-amino-acids, including the building blocks of naturally-occurring peptides and proteins including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V).

Non-limiting examples of nucleosides include adenosine, guanosine, cytidine, thymidine and uridine. Non-limiting examples of nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

Vitamins, include, but are not limited to, water-soluble vitamins such as thiamine, riboflavin, nicotinic acid, pantothenic acid, pyridoxine, biotin, folate, vitamin $B_{12}$ and ascorbic acid, fat-soluble vitamins such as vitamin A, vitamin D, vitamin E, and vitamin K.

Monosaccharides, include but are not limited to, D- or L-monosaccharides and whether aldoses or ketoses. Monosaccharides include, but are not limited to, triose, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Lipids, include, but are not limited to, triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

Preferably, the blood sample with added glyceraldehyde is used in a glucose assay. Glucose can be assayed according to any methods known in the art including the methods disclosed in U.S. Pat. Nos. 6,027,692, 5,843,692, 5,695,949, 5,645,710 and 5,037,738.

U.S. Pat. No. 6,027,692 discloses an integrated glycemic test system, consisting of (a) a first strip capable of reacting with glucose in a liquid sample, (b) a second strip capable of reacting with protein-bound glucose in a liquid sample, and (c) a single device having a spectrophotometer and a single receiving port capable of accepting the first and the second strips when inserted one at a time, so that (1) when the first strip is inserted into the receiving port, the spectrophotometer measures the glucose reaction on the first strip and the device displays the glucose concentration of the liquid sample, and (2) when the second strip is inserted into the receiving port, the spectrophotometer measures the protein-bound glucose reaction on the second strip and the device displays the protein-bound glucose concentration of the liquid sample.

U.S. Pat. No. 5,843,692 discloses a method for measuring a glucose concentration in whole blood using a reagent test strip having a matrix pad and a reflectance meter. The test strip is placed in the meter, and a blood sample is applied to the top surface of the pad. As the sample travels through the pad, glucose in the blood reacts with reagent in the pad to cause a change in reflectance of its bottom surface. An incubation period is initiated when the meter detects that at least a portion of the sample has reached the bottom surface. At the end of the incubation period, the reflectance of the bottom surface is measured and used to calculate the glucose concentration.

U.S. Pat. No. 5,695,949 discloses a method for determining integrated glycemic condition of a subject with a single test device responsive to a signal producing system indicative of glucose concentration and a signal producing system indicative of fructosamine concentration, consisting of the steps of: (a) applying a body fluid sample to a first test strip containing a signal producing system indicative of glucose concentration present in the body fluid sample; (b) applying a body fluid sample to a second test strip containing a signal producing system indicative of fructosamine concentration present in the body fluid sample; and (c) determining in either order (1) the glucose concentration and (2) the fructosamine concentration present in the body fluid sample applied to the first and second test strips, respectively, using a single test device having a glucose concentration determining means that is responsive to the signal producing system indicative of glucose concentration and a fructosamine concentration determining means that is responsive to the signal producing system indicative of fructosamine concentration, said test device preset to be responsive to only these two means, said test device further having an automatic determining means coupled to a display means and further having a receiving port for a test strip in connection with the automatic determining means; wherein the glucose concentration and the fructosamine concentration indicate integrated glycemic condition of a subject.

U.S. Pat. No. 5,645,710 discloses a method for the assay of glucose in aqueous media comprising: a) forming an electrolytic cell by bringing a redox electrode and a reference electrode into simultaneous contact with an aqueous medium containing KCl, phosphate buffer mixture, glucose oxidase, peroxidase, and 3,3',5,5'-tetramethylbenzidine dihydrochloride, said redox electrode comprising; an electrically conductive member, a redox membrane in direct contact with said electrically conductive member, said redox membrane comprising; a polymer matrix, said polymer matrix containing; a plasticizer, and a complex of 7,7,8,8-tetracyanoquinodimethane and tetrathiafulvalene wherein the complex comprises a complex having an ultraviolet absorption spectrum with broad absorption from about 340 nanometers to about 550 nanometers, said redox membrane having an electrical potential; and b) monitoring the electrical potential of said redox membrane until it is stable; and c) adding a sample containing glucose to said aqueous medium; and d) observing a change of the electrical potential of said redox membrane.

U.S. Pat. No. 5,037,738 discloses a method for the simultaneous determination of glucose and urea in a specimen with a single reagent system. A reagent system containing a reactant for each of glucose and urea to be determined is added to a specimen. The reagent system is reacted with the specimen such that each of glucose and urea react with their respective reactant simultaneously. Each reactant is selected such that it is capable of giving an absorbance band for glucose and urea which permits their simultaneous determination. The change in absorbance or fluorescence of the resulting reaction mixture is monitored at a plurality of wavelengths which are characteristic for each of glucose and urea.

The blood sample with added glyceraldehyde can also be used in other metabolism assays including assays for native prothrombin (U.S. Pat. No. 5,935,802), particularly protein and cellular concentrations (U.S. Pat. No. 5,583,432), an endotoxin (U.S. Pat. No. 5,286,625) and fibrinogen (U.S. Pat. No. 5,156,974). Preferably, the metabolism assay is used in assaying ions such as sodium, potassium, chloride and calcium ions, glucose, creatinine, urea, bilirubin, albumin, alkaline phosphatase activity, AST, total protein and total $CO_2$.

Also preferably, the metabolism assay is operated on an automated analyzer such as Ortho-Clinical Diagnostics Vitros 250, Dade Behring RxL, Hitachi 747 analyzer, an automated hematology analyzer (SE-9000) (Takekawa et al., *Acta Haematol.*, 100(3):130–6 (1998)), an automated, and computer-assisted luminometer (LB 950, Berthold, Wildbad, Germany) (Carulli et al., *Int. J. Clin. Lab. Res.*, 25(4):216–21 (1995)), Miles H*3 blood analyzer (Brugnara et al., *Am. J. Clin. Pathol.*, 102(5):623–32 (1994)), an automated tabletop blood biochemical analyzer for the veterinary clinical pathology laboratory (Sallee et al., *J. Am. Vet. Med. Assoc.*, 196(2):307–12 (1990)), Technicon H-1 automated hematology analyzer (Banez and Bacaling, *Arch. Pathol., Lab. Med.*, 112(9):885–8 (1988)) or analyzers disclosed in U.S. Pat. Nos. 5,930,791, 4,135,883 and 4,030,888.

U.S. Pat. No. 5,930,791 discloses a computerized blood analyzer system. The system includes a clinical analyzer CU and a blood analyzer AU. The clinical analyzer has a computer which issues commands and instructions to the AU as desired. These commands and instructions include retrieval and storage commands and instructions. The blood analyzer unit AU is electronically connected to the CU and operates upon the commands and instructions of the CU. The AU generates test results which are stored in the computer. The computer has storage media for storing the results. The storage media comprises an aggregate database which includes at least two parts, namely a working database and an archived database. It is preferable in many case for the aggregate database to include a back-up database. Each of the databases stores the data in similar data fields, organization and structure comprising symmetrical-like databases. This enables a single set of commands and instructions to store and retrieve the data.

U.S. Pat. No. 4,135,883 discloses an apparatus for performing chemical tests comprising: (a) a centrifuge having a rotor, said rotor including cuvette-retaining means; (b) a cuvette having a test chamber portion therein and test information coding thereon, said cuvette being mountable into said cuvette-retaining means; (c) a spectrophotometer mounted on said centrifuge and adapted to read the test chamber portion of said cuvette; (d) means for reading the test information coding on said cuvette, said code reading means being mounted on said centrifuge; (e) and means for receiving the signal from said code reading means and from said spectrophotometer and for displaying the test result appropriate for said test information coding.

U.S. Pat. No. 4,030,888 discloses a fully automatic system for determining the seven blood parameters, red blood counts (RBC), hematocrit (HCT), white blood counts (WBC), mean corpuscular hemoglobin (MCH), mean corpuscular volume (MCV) and mean corpuscular hemoglobin concentration (MCHC). The blood sample collected is divided into two solutions, one for use in red blood counts and subjected to the calorimetric analysis for HGB determination and the other for use in white cell counts. A portion of the RBC solution is subjected to the double blood dilution and it enters a red cell counting portion. The peak value of electrical pulses supplied by said counting portion is indicative of the hematocrit. These data are used by preset arithmetic circuits to determine MCH, MCV and MCHC. White blood corpuscles are counted by a counting means of the same structure as that of the red cell counting portion. The flow of a diluent and the blood solution starting from the introduction of the sample, to counting portions, means for determination, and to the outlets are controlled by the supply of either vacuum or pneumatic pressure into two rotary proportioning cocks and chambers positioned upstream or downstream thereof.

E. Kits, Combinations and Combinatorial Methods

In one aspect, a kit for stabilizing glucose level in a blood sample is provided, which kit comprises: a) an effective amount of glyceraldehyde; and b) an instruction indicating that said kit is used for stabilizing glucose level in a blood sample. Preferably, the kit further comprises a blood collection and/or a blood storage device.

In another aspect, a combination for stabilizing glucose level in a blood sample is provided, which combination comprises: a) an effective amount of glyceraldehyde; and b) an effective amount of an anti-glycolytic agent that is not glyceraldehyde.

Any glyceraldehyde, including the ones described in Section B, can be used. Any anti-glycolytic agents known in the art can be used. For example, Lonidamine [1-(2,4-chlorobenzyl)-1H-indazol-3-carboxylic acid] (Floridi et al., *J. Nat. Cancer. Inst.*, 66(3):497–9 (1981)) and Arenaemycin (pentalenolactone) (Hartmann et al., *FEBS Lett.*, 93(2):339–42 (1978)) can be used. In addition, anti-glycolytic agents disclosed in U.S. Pat. Nos. 5,955,371, 4,933,145, 4,780,419, 4,833,090 and 4,054,488 can be used.

U.S. Pat. No. 5,955,371 discloses an article of manufacturing comprising, a blood collection tube containing granulated additive particles wherein each particle comprises a fluoride salt component and an anticoagulant component wherein said particles have a mesh size from 130 to 350. U.S. Pat. No. 5,955,371 also discloses a granulated additive particle formulation for use in blood collection tubes to minimize glycolysis and blood coagulation with low hemolysis, comprising a fluoride salt component and an anticoagulant component, wherein each particle has a mesh size from 130 to 350.

U.S. Pat. No. 4,933,145 discloses an article of manufacture comprising a blood-collection tube containing an organic acid in an amount effective to adjust pH of blood to be collected in said tube to a level between 5.0 and 7.0 and to inhibit glycolysis of the blood, said organic acid being selected from the group consisting of citric acid, acetic acid, malonic acid and maleic acid.

U.S. Pat. No. 4,780,419 discloses a method of inhibiting glycolysis in blood samples which comprises adding an acid to the blood sample to adjust pH of the blood to a level between 5.0 and 7.0.

U.S. Pat. No. 4,833,090 discloses a method of determining the glucose content of a sample of whole blood collected in a container which comprises including in said container an isomer of glucose capable of replacing glucose in the metabolism of blood cells, and isomer being present in an amount equal to at least 0.1 mg per ml of sample, and thereafter determining the glucose content of said sample.

U.S. Pat. No. 4,054,488 discloses tris-iodoacetate, a salt of bromoacetic acid or a salt of chloroacetic acid as a glucose preservative in blood sample.

In still another aspect, a method for stabilizing glucose level in a blood sample is provided, which method comprises adding an effective amount of glyceraldehyde and an effective amount of an anti-glycolytic agent that is not glyceraldehyde to a blood sample, whereby glucose level in said blood sample remains substantially constant for a period of time. The above described glyceraldehyde and anti-glycolytic agents can be used in the method. The glyceraldehyde and anti-glycolytic agents can be added to the blood sample simultaneously or sequentially.

In yet another specific embodiment, a combination for preserving a blood sample for a further analysis is provided, which combination comprises: a) an effective amount of glyceraldehyde; and b) an effective amount of a blood-preserving agent. Any glyceraldehyde, including the ones described in Section B, can be used. Any blood-preserving agents known in the art can be used. For example, blood-preserving agents disclosed in U.S. Pat. Nos. 4,356,172 and 4,040,785, EP 0,367,271 and JP 61,015,838 can be used.

U.S. Pat. No. 4,356,172 discloses an erythrocyte preservative which contains an erythrocyte membrane strengthening agent, optionally a purine base and/or purine nucleoside and optionally an anticoagulant. U.S. Pat. No. 4,040,785 discloses a preservative reagent consisting of an aqueous mixture of a mono-, di- or trisaccharide component and formaldehyde.

EP 0,367,271 discloses an improved red blood cell preservative solution containing at least one component selected from the group consisting of glutathione, glutamine, cacodylic acid, cacodylates, barbituric acid, barbiturates, Good's buffer and Britton & Robinson's buffer in an amount of 1 to 200 mM.

JP 61,015,838 discloses a blood preservative obtained by using an acidic amino acid, e.g. aspartic acid or glutamic acid, and/or a salt thereof, e.g., an alkali metal salt such as Na salt or a salt with a mineral acid such as HCl, as a principal component, and if necessary together with a neutral amino acid, e.g., glycine or alanine, aromatic amino acid, e.g., phenylalanine, or basic amino acid, e.g., lysine, in a small amount. The addition of the above-mentioned component protects or strengthens the erythrocytic membranes and prevents the hemolysis of the preserved blood. The concentration of the acidic amino acid and/or salt thereof in the preservative is preferably 10–500 mmol/l expressed in terms of the acidic amino acid. A blood coagulation inhibitor, e.g., a disaccharide, polyhydric alcohol or citric acid, may be added thereto as an erythrocytic preservative component if necessary. The resultant preservative can be suitably used for warm-blooded animals.

In yet another specific embodiment, a method for preserving a blood sample for a further analysis is provided, which method comprises adding an effective amount of glyceraldehyde and an effective amount of a blood-preserving agent to a blood sample, whereby the quality of said blood sample is substantially preserved for a further analysis. The above described glyceraldehyde and blood-preserving agents can be used in the method. The glyceraldehyde and blood-preserving agents can be added to the blood sample simultaneously or sequentially.

The following example is included for illustrative purposes only and is not intended to limit the scope of the invention.

F. EXAMPLES

1. Methods

Subjects

Whole blood specimens collected in tubes containing sodium heparin as anticoagulant were obtained from healthy adult volunteers or from adult diabetic patients visiting an outpatient clinic, after obtaining informed consent. Specimens were employed for experimentation within one hour of collection. In a few experiments, whole blood heparinized specimens arriving at the clinical laboratory for analysis for glucose and other common analytes were mixed, and aliquots removed for experimental purposes. These studies were conducted in accordance with a protocol approved by the Human Studies Committee of Washington University.

Experimental Design

Aliquots of heparinized whole blood (0.96 mL) were pipetted into microfuge tubes containing 0.040 mL of saline or anti-glycolytic agent in saline. Anti-glycolytic agents were prepared as 250 mmol/L stock solutions within one hour of use. At various times plasma was prepared from incubations by centrifugation at 8000×G for two minutes; plasma was decanted to 12×75 mm tubes and stored frozen until analysis. All incubations of whole blood were conducted at room temperature (23°) on a rotating table shaker, which kept the cells in dispersed suspension. d,1-glyceraldehyde, methylgloxal, d-glyceraldehyde, glycolaldehyde and dihydroxyacetone were obtained from Sigma Chem Co. (St. Louis, Mo.). 1-glyceraldehyde was obtained from Fisher Scientific (Pittsburgh, Pa.).

Analytical Procedures

Glucose analyses were routinely performed on a Cobas-MIRA analyzer (Roche Diagnostic Systems, Montclair, N.J.), employing reagents based on glucose oxidase, manufactured by Sigma Diagnostics (St. Louis, Mo.). In some experiments, glucose and many other common laboratory analyses were performed on a Vitros 250 Analyzer (Ortho-Clinical Diagnostics, Rochester, N.Y.), a Hitachi 747 Analyzer (Boehringer-Mannheim Corp., Indianapolis, Ind.) and a RxL Analyzer (Dade Behring, Inc. Newark, Del.).

Statistical Analysis

All results are stated as means plus/minus one standard deviation, unless otherwise stated. Correlative studies are reported graphically, after calculation of at least squares linear regression relationship.

2. Results

Stabilization of Blood Glucose Levels by d,1-Glyceraldehyde (d,1-GA)

Whole heparinized blood was incubated for 0–8 hours in the presence of 10 mmol/L d,1-GA, and the glycolytic loss of glucose followed over time (FIG. 1). A linear decrease in glucose concentration was evident in incubations without additive, with 38% of the initial glucose concentration lost in 8 hours (0.23 mmol/L per hour). In incubations containing d,1-GA, glucose concentrations remained nearly constant throughout the 8 hour period, with loss at 8 hours of only 2%. Thus d,1-GA appeared to be highly effective in preventing loss of glucose in whole blood for up to 8 hours. The presence of d,1-GA did not promote visible hemolysis.

Dose-Dependent Stabilization Glucose Levels by d,1-GA

Figure 2:
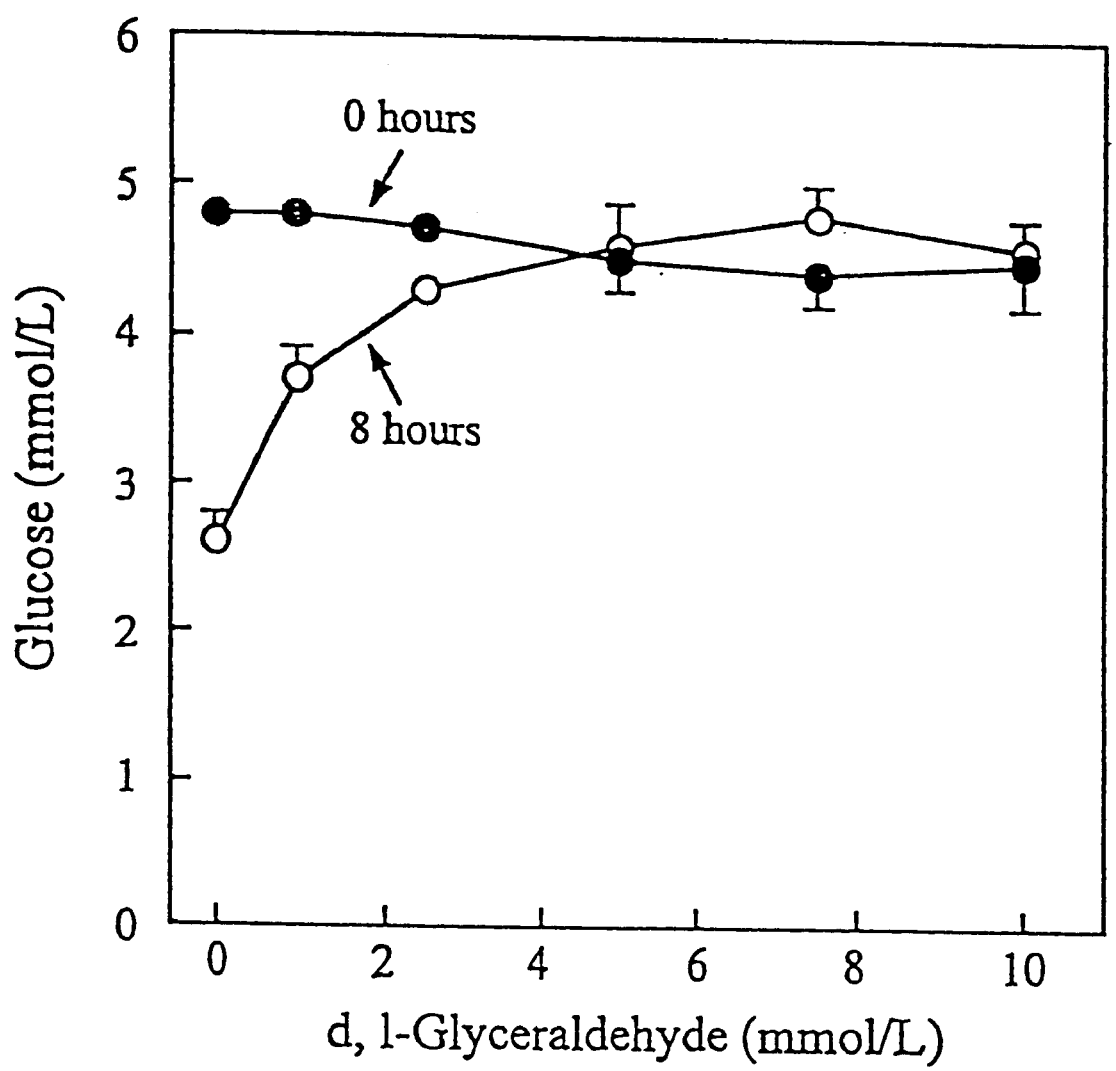
FIG. 2: Concentration dependence of the glucose preservation action of d,1-GA. Two curves are presented: one curve presents data at varied d,1-GA concentrations at the start of the experiment ("0 hours") and the other curve after 8 hours of incubation at room temperature ("8 hours"). Error bars, when error exceeds the size of the symbols used, are shown for triplicate replicates.

Whole heparinized blood was incubated for 8 hours in the presence of 0–10 mmol/L d,1-GA (FIG. 2). Similar to preceding experiments, glucose concentrations declined from 4.8±0.1 mmol/L to 2.6±0.2 mmol/L (46% decline) when no d,1-GA was present, but increasing concentrations of d,1-GA effectively preserved glucose levels so that at 5 mmol/L d,1-GA decreases in glucose were nearly completely eliminated (residual glucose 4.6±0.3 mmol/L at 8 hours). The concentration of d,1-GA that reduced glycolytic loss by half was approximately 0.9 mmol/L. The presence of d,1-GA did not appear to interfere in the glucose assay at any of the concentrations examined (FIG. 2).

Efficacy of d,1-GA in Patient Specimens

Figure 3:
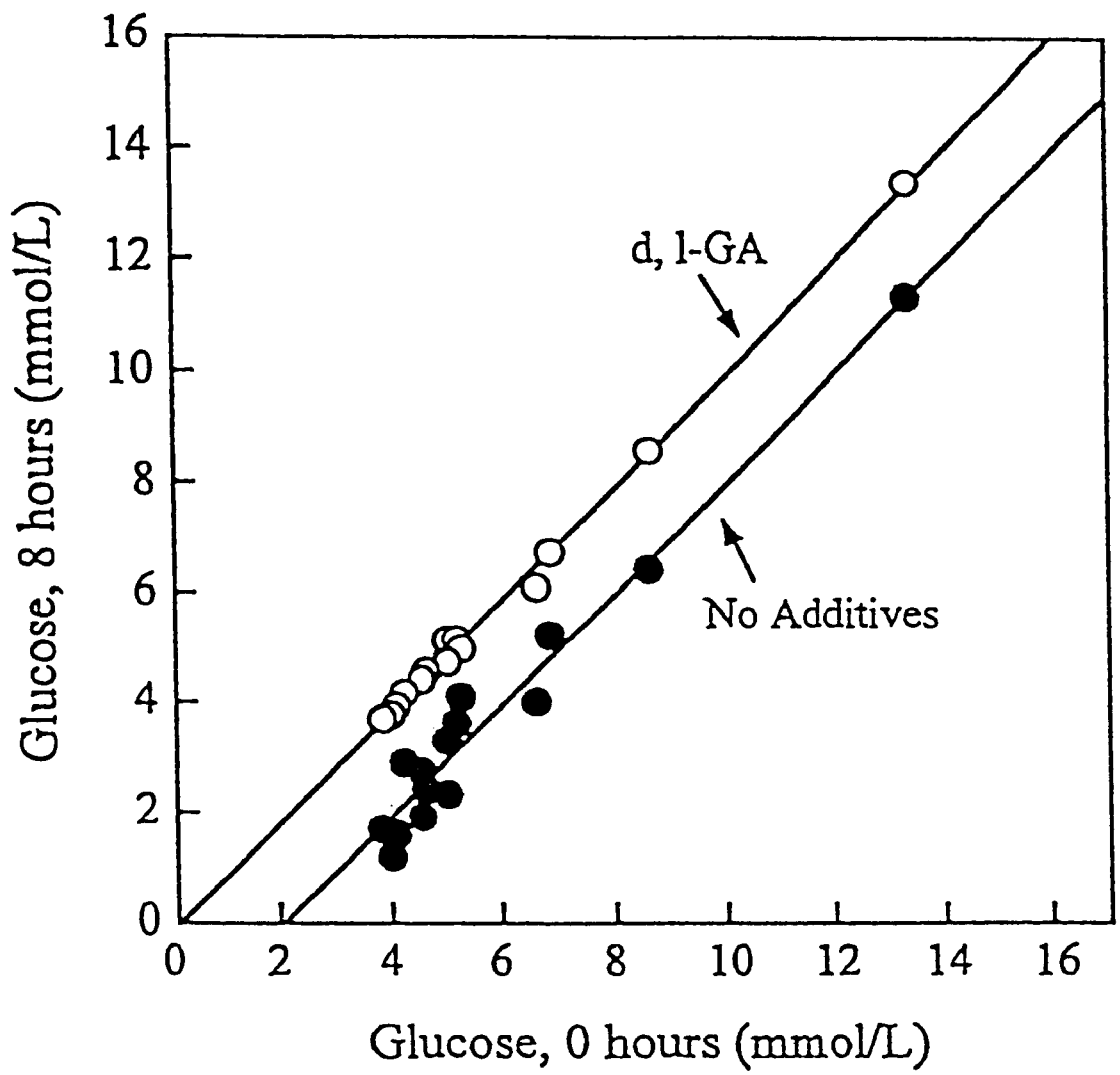
FIG. 3: Glycolytic loss in a range of patient specimens. Glucose concentration at the start of the experiment is plotted on the horizontal axis, and glucose concentrations after 8 hours incubation on the vertical axis. Incubations containing either 10 mmol/L d,1-GA (○-○) or no additives (●-●) are plotted on separate curves.

Specimens arriving at the clinical laboratory for glucose and other common laboratory analyses were split into three aliquots; one was analyzed immediately to establish the initial glucose concentration in each specimen, one was incubated for 8 hours without additive, and the third aliquot was incubated for 8 hours in the presence of 10 mmol/L d,1-GA. Results are presented by plotting initial glucose concentration against glucose concentrations either in the presence or absence of d,1-GA (FIG. 3). The line generated with incubations without additive has a slope of 1.01 and an intercept of −2.2 mmol/L, indicating that 8 hours of incubation reduced glucose concentrations an average of 2.2 mmol/L regardless of starting concentration. The relationship of initial glucose to glucose concentration after 8 hours of incubation in the presence of d,1-GA also yielded a slope of 1.01, but the intercept was only 0.3 mmol/L, indicating that d,1-GA reduced the extent of glucose loss more than 7-fold compared with the absence of d,1-GA. Further, d,1-GA appeared to be equally effective regardless of the starting glucose concentration, which ranged from 3.9 to 13.4 mmol/L.

Effect of d,1-GA On Erythrocyte Potassium Homeostasis

Some anti-glycolytic agents so effectively inhibit erythrocyte metabolism of glucose, that the cells are deprived of sufficient energy to maintain the potassium gradient between plasma and intracellular fluid, resulting in significant increases in plasma potassium concentrations. The time course of potassium concentration changes was followed for 8 hours in whole blood incubations under three conditions; 1) incubation at room temperature (without additions), 2) incubation at room temperature with 10 mmol/L d,1-GA, and 3) incubation at 4° C. (without additions). In room temperature incubations without additive, potassium decreased modestly from 4.0±0 mmol/L at 0 hours to 3.5±0.1 mmol/L at 8 hours. Incubation for 8 hours in the presence of d,1-GA caused an increase of similar magnitude (to 4.5±0 mmol/L). In contrast, incubation at 4° C., which has been advocated as an effective way to prevent glucose loss for short periods (Lin et al., *Clin. Chem.*, 22:2031–3 (1976)), caused an increase to 6.0±0.1 mmol/L.

Glucose Preservation Activity of Related Compounds

Several compounds related biochemically or structurally to d,1-GA were tested for ability to preserve specimen glucose; incubations without inhibitor and with d,1-GA were included for comparison (Table I). All compounds were tested at a final concentration of 10 mmol/L, and incubations were conducted at 0 hours and 8 hours for each compound. Only the d and l stereoisomers of glyceraldehyde (d-GA and 1-GA) prevented glucose loss. The inhibition of d-GA was only partly effective, reducing glucose loss from 41% (no additions) to 17%. Loss of glucose was completely prevented by 1-GA. The partial inhibition of d-GA could have been due to small contamination of the d-GA preparation with the 1 isomer, and the efficacy of d,1-GA could be due entirely to the action of the 1 isomer in this preparation. To test this possibility, an experiment varying the concentration of 1-GA was performed in analogy with the earlier experiment varying the d,1-GA concentration (see above). If 1-GA is the active portion of the d,1-GA mixture (and d-GA is inert), then the concentration of 1-GA needed to inhibit glycolysis will be half that of d,1-GA. The concentration that reduced glucose loss by 50% was approximately 0.65 mmol/L, which was close to half the d,1-GA concentration needed (see above). Further, 2.5 mmol/L 1-GA was nearly completely effective in eliminating glycolytic loss during an 8 hour incubation (data not shown), compared to twice that concentration of d,1-GA needed for comparable influence. These results were interpreted to suggest that the antiglycolytic action of d,1-GA was due to 1-GA component of the racemic mixture.

TABLE I

Glucose Preservation Activity of Compounds Related to d,1-GA

| Agent[a] | Glucose at 0 Hours (mmol/L) | Glucose at 8 hours (mmol/L) | Decrease |
|---|---|---|---|
| No Additions | 4.8(0.3) | 2.8(0.3) | 41% |
| d,1-GA | 4.7(0.2) | 4.8(0.1) | 0% |
| d-GA | 4.7(0.1) | 3.9(0.1) | 17% |
| 1-GA | 4.8(0.1) | 4.8(0.1) | 0% |
| Methylglyoxal | 4.5(1.0) | 2.6(0.2) | 43% |
| Glyceric Acid | 4.7(0.1) | 2.7(0.2) | 42% |
| Dihydroxyacetone | 4.5(0.1) | 2.4(0.1) | 46% |
| Glycolaldehyde | 4.8(0.1) | 2.3(0.1) | 52% |
| L-Sorbose | 5.0(0.1) | 3.1(0) | 38% |

[a]All compounds were present at a final concentration of 10 mmol/L.

Clinical Diagnostics Vitros 250, Dade Behring RxL and Hitachi 747 analyzers. The analytes tested were those in the standard "basic metabolic panel/comprehensive metabolic panel" (Table II). Glucose results were similar on all three analyzers, which suggested that 1-GA and d,1-GA do not effect either glucose oxidase methods (Vitros 250 and Hitachi 747) or methods based on hexokinase (Dade Behring RxL). The other analytes examined were also free of significant interference from either 1-GA or d,1-GA, except creatinine. Creatinine analyses on the Vitros 250 and Hitachi 747 (both enzymatic methods) were not influenced by the presence of GA, but the alkaline picrate method of the Dade Behring RxL was highly susceptible to positive interference by either form of GA (Table II). AST results were modestly depressed in the presence of GA on all three analyzers, with greater decreases observed on the Dade Behring RxL, and lesser effects in specimens treated with 1-GA, but these decreases were too small to reach statistical significance (Table II).

TABLE II

Effect of d,1-GA or 1-GA on Glucose and other Analytes, Measurd on Three Analysers

| | Vitros 250 | | | Dade Behring RxL | | | Hitachi 747 | | |
|---|---|---|---|---|---|---|---|---|---|
| Analyte | NoAdd | d, 1-GA | 1-GA | NoAdd | d, 1-GA | 1-GA | NoAdd | d, 1-GA | 1-GA |
| Glucose mmol/L | 11.0 (6.4) | 10.9 (6.5) | 10.9 (6.5) | 10.5 (6.2) | 10.5 (6.2) | 10.6 (6.3) | 10.6 (6.1) | 10.5 (6.0) | 10.5 (5.9) |
| Sodium mmol/L | 142 (2) | 142 (1) | 143 (1) | 140 (2) | 140 (2) | 140 (2) | 139 (2) | 139 (2) | 139 (2) |
| Potassium mmol/L | 4.5 (1.1) | 4.6 (1.2) | 4.6 (1.1) | 4.5 (1.1) | 4.5 (1.2) | 4.5 (1.1) | 4.6 (1.0) | 4.6 (1.1) | 4.6 (1.1) |
| Chloride mmol/L | 110 (4) | 110 (5) | 109 (4) | 105 (3) | 105 (4) | 105 (3) | 105 (3) | 105 (3) | 105 (3) |
| Total $CO_2$ mmol/L | 26 (3) | 25 (4) | 25 (4) | 25 (3) | 24 (2) | 24 (3) | 26 (3) | 25 (3) | 26 (3) |
| Creatinine µmol/L | 80 (18) | 71 (18) | 80 (18) | 88 (18) | 327 (35)[b] | 194 (27)[b] | 97 (18) | 80 (9) | 88 (18) |
| Urea µmol/L | 6.4 (2.8) | 6.4 (2.8) | 6.4 (2.8) | 5.4 (2.5) | 5.4 (2.5) | 5.4 (2.5) | 5.7 (2.5) | 5.7 (2.5) | 5.7 (2.5) |
| Calcium µmol/L | 2.1 (0.1) | 2.1 (0.1) | 2.2 (0.1) | 2.1 (0.1) | 2.2 (0.1) | 2.2 (0.1) | 2.1 (0.1) | 2.1 (0.1) | 2.1 (0.1) |
| Bilirubin µmol/L | 15.4 (10.3) | 15.4 (10.3) | 15.4 (10.3) | 6.8 (3.4) | 8.6 (1.7) | 6.8 (1.7) | 5.1 (1.7) | 6.8 (3.4) | 6.8 (3.4) |
| Albumin g/L | 38 (2) | 38 (2) | 38 (2) | 37 (3) | 37 (3) | 37 (3) | 37 (2) | 36 (2) | 37 (2) |
| Protein g/L | 67 (3) | 65 (4) | 66 (4) | 65 (2) | 65 (3) | 66 (2) | 64 (2) | 63 (3) | 63 (3) |
| Alk Phos U/L | 76 (19) | 76 (19) | 77 (19) | 78 (12) | 76 (14) | 76 (14) | 85 (6) | 83 (7) | 84 (7) |
| AST U/L | 37 (18) | 33 (14) | 35 (15) | 31 (22) | 23 (14) | 26 (15) | 32 (21) | 25 (16) | 29 (20) |

[a]All results are expressed as means with SD in parentheses.
[b]$p < 0.001$

Effect of d,1-GA and 1-GA on Common Clinical Chemical Tests

The potential for d,1-GA and 1-GA to interfere in testing for commonly ordered co-analytes was investigated by drawing blood from six diabetic patients in a clinic setting and adding to aliquots either 10 mmol/L d,1-GA, 5 mmol/L 1-GA or the same volume of saline. The aliquots were immediately centrifuged and plasma decanted for analysis on three common laboratory automated systems; Ortho- 3. Discussion Considerable effort has been expended in the past to find a highly effective preservative of glucose for blood collection that does not interfere in other common clinical chemical tests, does not cause hemolysis or other loss of cellular integrity, is non-toxic, is stable for storage at room temperature, and is inexpensive. Glyceraldehyde, and specifically 1-GA, seems to meet these criteria better than any currently available alternative. Specimens containing 1-GA were suitable for most common clinical chemical determinations, though careful evaluation will be needed in individual laboratories to determine the potential for interference in such methodologies as the alkaline picrate method for creatinine. Unlike the most prevalently employed glucose preservation agent, fluoride ion, 1-GA does not cause hemolysis, and potassium concentrations in plasma from GA-treated specimens remain suitable for assessment of potassium homeostasis for up to eight hours. From the standpoint of stability and toxicity, 1-GA seems ideal as an additive since it is a natural product with a long shelf life. Since 1-GA is fully effective at concentrations as low as 2.5 mmol/L, the actual amount of 1-GA needed for the standard evacuated 7 mL collection tube is 1.58 mg. This small dose limits the expense of use of 1-GA, and eliminates the potential that volume dilution of the specimen by the additive might decrease glucose and other determinations, in contrast to the equivalent fluoride/oxalate tube, which contains more than 50 mg of additive. Volume dilution of specimen by additive become more important when collection tubes are only partially filled.

Prevalent approaches for minimizing glycolytic loss of glucose have considerable limitations. The use of fluoride or iodoacetate to inhibit cellular glycolytic enzymes is only partially effective; though significantly decreased, glycolysis continues in the presence of either agent, particularly in the first few hours after collection (Chan et al., Clin. Chem., 35:315–7 (1989); and Meites and Saniel-Banrey Clin. Chem., 25:531–4 (1979)). Iodoacetate interferes in at least some methods of glucose analysis (Hall and Cook Clin. Chem., 28:387–8 (1982)). Specimens collected in standard fluoride/oxalate tubes are invariably hemolyzed, which makes them unsuitable for analysis of other important analytes that are frequently requested in conjunction with glucose, such as potassium. The use of mannose as an anti-glycolytic agent has been hampered by reports of interference of mannose in several glucose methods (Ho et al., Clin. Chem., 37:477 (1991); and van Dijck and Lievens M M. Clin. Chem., 37:1308–9 (1991)). Mannose also was judged unsuitable for preservation of specimens for electrolyte analysis due to appearance of cellular potassium in the plasma phase during storage (Chan et al., Clin. Chem., 38:411–3 (1992)). Immediate cooling of specimens and transportation on ice effectively preserves glucose concentrations (Lin et al., Clin. Chem., 22:2031–3 (1976)), but imposes additional costs and burden on the transportation process. Because metabolism is reduced by cooling, cellular potassium rapidly diffuses into the plasma phase of whole blood specimens which significantly increased plasma potassium concentrations after one hour (Lin et al., Clin. Chem., 22:2031–3 (1976)). The use of near-patient analytical devices to measure glucose immediately after specimen collection effectively eliminates glycolytic loss, but these analytical devices are typically very expensive to operate and place a considerable burden on patient care staff. Glucose meters are a prevalent and relatively inexpensive example of this approach, but offer only glucose determinations (Dietzler and Smith, Carbohydrates (In: Sonnenwirth A C, Jarett L, eds. Gradwohl's Clinical Laboratory Methods and Diagnosis. Vol I, 8$^{th}$ ed. St. Louis, Toronto, London: CV Mosby Co., 1980:210–49).

The anti-glycolytic effect of 1-GA has been previously noted, but 1-GA has never been tested as an additive for preservation of blood specimens for glucose analysis (for review see Best and Thornalley, Biochem. Pharmacol., 57:583–8 (1999)). The ability of 1-GA to inhibit gluconeogenesis from d-GA in slices of rat kidney cortex was documented in 1966 (Krebs and Lund, Biochem. J., 98:210–4 (1966)). Thornalley and Stern noted 1-GA inhibition of lactate/pyruvate formation from radioactive glucose in erythrocytes, but did not measure glucose concentrations in blood or plasma in their experiments (Thornalley and Stern, Biochem. Biophys. Acta, 804:308–23 (1984)). Glyceraldehyde has been investigated as an agent promoting insulin secretion from isolated pancreatic islets (Best and Thornalley, Biochem. Pharmacol., 57:583–8 (1999)); both d-GA and 1-GA were effective in promoting secretion. The action of d-GA and 1-GA was related to auto-oxidation to methylglyoxal, which is a highly reactive inhibitor of many cellular functions.

The mechanism of 1-GA inhibition of glycolysis in erythrocytes has not been fully established. 1-GA is poorly metabolized (Best and Thornalley, Biochem. Pharmacol., 57:583–8 (1999); and Krebs and Lund, Biochem. J., 98:210–4 (1966)), through conversion to glycerol (Thornalley and Stern, Biochem. Biophys. Acta, 804:308–23 (1984)). Hexokinase has been proposed as the site of inhibition by 1-GA (Thornalley and Stern, Biochem. Biophys. Acta, 804:308–23 (1984)), through condensation with dihydroxyacetone phosphate to form sorbose-1-phosphate, which is an inhibitor of hexokinase (Goto et al., Am. J. Vet. Res., 55:291–4 (1994)). Based on this hypothesis, I anticipated that L-sorbose might mimic the anti-glycolytic activity of 1-GA, through cellular conversion to sorbose-1-phosphate, but sorbose was not effective at concentrations similar to whose of d,1-GA which were effective in preserving glucose concentrations. It is also possible that 1-GA inhibits glycolysis through autooxidation to methylglyoxal or pyruvaldehyde, which are known to form covalent adducts with proteins and to inhibit many cellular processes (Best and Thornalley, Biochem. Pharmacol., 57:583–8 (1999)). However, results from my study argue against this mechanism. Both d-GA and 1-GA readily autooxidize, but only 1-GA seemed to be the active agent in my experiments. Methylglyoxal and related compounds were ineffective as glucose preservation agents when incubated with erythrocytes at the same concentrations that was effective for 1-GA. Further studies are needed to determine the metabolic fate of 1-GA in erythrocytes and to determine the site of inhibition of glycolysis by 1-GA or a metabolic product.

Since modifications will be apparent to those of skill in this art, it is intended that this invention be limited only by the scope of the appended claims.

What is claimed is:

1. A method for stabilizing glucose level in a blood sample, which method comprises adding an effective amount of glyceraldehyde to a blood sample, whereby glucose level in said blood sample remains substantially constant for a period of time.

2. The method of claim 1, wherein the glyceraldehyde is a racemic mixture of d,1-glyceraldehyde.

3. The method of claim 1, wherein the glyceraldehyde is d-glyceraldehyde or 1-glyceraldehyde.

4. The method of claim 1, wherein the glyceraldehyde is 1-glyceraldehyde.

5. The method of claim 2, wherein the final concentration of the racemic mixture of d,1-glyceraldehyde in the blood sample is from about 0.9 to about 20 mM.

6. The method of claim 5, wherein the final concentration of the racemic mixture of d,l-glyceraldehyde in the blood sample is from about 5 to about 10 mM.

7. The method of claim 4, wherein the final concentration of the l-glyceraldehyde in the blood sample is from about 0.65 to about 10 mM.

8. The method of claim 7, wherein the final concentration of the l-glyceraldehyde in the blood sample is from about 2.5 to about 5 mM.

9. The method of claim 1, wherein the blood sample is a whole blood, plasma or serum sample.

10. The method of claim 9, wherein the whole blood sample is a heparinized whole blood sample.

11. The method of claim 1, wherein the starting glucose concentration in the blood sample is from about 0 to about 100 mM.

12. The method of claim 11, wherein the starting glucose concentration in the blood sample is from about 3.9 mM to about 13.4 mM.

13. The method of claim 1, wherein the starting glucose concentration does not decrease by more than 5%.

14. The method of claim 1, wherein the starting glucose concentration does not decrease by more than 2%.

15. The method of claim 1, wherein the glucose level in the blood sample remains substantially constant for at least about 16 hours.

16. The method of claim 1, wherein the glucose level in the blood sample remains substantially constant for at least about 8 hours.

17. The method of claim 1, wherein the blood sample with the added glyceraldehyde is subjected to a metabolism assay.

18. The method of claim 17, wherein the metabolism assay is for an analyte selected from the group consisting of an ion, glucose, creatinine, urea, bilirubin, albumin, alkaline phosphatase activity, aspartate aminotransferase, total protein and total $CO_2$.

19. The method of claim 18, wherein the ion to be assayed is selected from the group consisting of a sodium, a potassium, a chloride and a calcium ion.

20. The method of claim 17, wherein the metabolism assay is operated on an automated analyzer.

21. The method of claim 20, wherein the automated analyzer is selected from the group consisting of Cobas-MIRA analyzer, Ortho-Clinical Diagnostics Vitros 250, Dade Behring RxL and Hitachi 747 analyzer.

22. A method for stabilizing glucose level in a blood sample, which method comprises adding an effective amount of glyceraldehyde and an effective amount of an anti-glycolytic agent that is not glyceraldehyde to a blood sample, whereby glucose level in said blood sample remains substantially constant for a period of time.

23. A method for preserving a blood sample for a further analysis, which method comprises adding an effective amount of glyceraldehyde and an effective amount of an a blood-preserving agent to a blood sample, whereby the quality of said blood sample is substantially preserved for a further analysis.

* * * * *